United States Patent
Schriefl (10) Patent No.: US 10,856,811 B2
(45) Date of Patent: Dec. 8, 2020

(54) AUTOMATED DIAGNOSIS-ASSISTING MEDICAL DEVICES UTILIZING RATE/FREQUENCY ESTIMATION

(71) Applicant: CSD LABS GMBH, Graz (AT)

(72) Inventor: Andreas J. Schriefl, Graz (AU)

(73) Assignee: CSD LABS GMBH, Graz (AT)

( * ) Notice: Subject to any disclaimer, the term of this patent is extended or adjusted under 35 U.S.C. 154(b) by 600 days.

(21) Appl. No.: 14/209,919

(22) Filed: Mar. 13, 2014

(65) Prior Publication Data

US 2014/0276132 A1    Sep. 18, 2014

Related U.S. Application Data

(60) Provisional application No. 61/787,998, filed on Mar. 15, 2013.

(51) Int. Cl.
 *A61B 5/00* (2006.01)
 *A61B 7/04* (2006.01)
 (Continued)

(52) U.S. Cl.
 CPC .......... *A61B 5/7203* (2013.01); *A61B 5/0022* (2013.01); *A61B 5/0205* (2013.01);
 (Continued)

(58) Field of Classification Search
 CPC ......... A61B 5/0205; A61B 7/04; A61B 5/024; A61B 5/0816; A61B 7/003; A61B 5/7235; A61B 5/72; A61B 7/02
 See application file for complete search history.

(56) References Cited

U.S. PATENT DOCUMENTS

| | | | |
|---|---|---|---|
| 4,403,184 A | | 9/1983 | Witt |
| 4,958,638 A | * | 9/1990 | Sharpe ................ A61B 5/0205 |
| | | | 600/407 |

(Continued)

FOREIGN PATENT DOCUMENTS

| | | |
|---|---|---|
| EP | 0 435 950 B1 | 8/1996 |
| EP | 2 692 294 A1 | 5/2014 |

(Continued)

OTHER PUBLICATIONS

Liang, H. et al.: *Heart Sound Segmentation Algorithm Based on Heart Sound Envelogram*; Computers in Cardiology, vol. 24, pp. 105-108 (1997) (4 pages).

(Continued)

*Primary Examiner* — Christian Jang
*Assistant Examiner* — Karen E Toth
(74) *Attorney, Agent, or Firm* — Nixon Peabody LLP (57) ABSTRACT

A method for processing a quasi-periodic signal includes receiving a representation of a quasi-periodic signal and removing a DC component from the received signal to produce a purely time-varying signal. The time-varying signal is filtered to produce a pre-processed signal and at least a portion of a representation of the pre-processed signal is auto-correlated with itself. A corresponding auto-correlation output is stored in a memory device for the at least portion of the representation of the pre-processed signal. A biphasic tapering function is applied to the auto-correlation output, the tapering function including a time constant parameter that is a function of the quasi-periodic signal and producing a first maximum. A representation, based on the first maximum, is stored in the memory device as an indication of a rate or a frequency of the quasi-periodic signal.

16 Claims, 7 Drawing Sheets

(51) Int. Cl.
- *G06K 9/00* (2006.01)
- *A61B 5/0205* (2006.01)
- *A61B 7/00* (2006.01)
- *A61B 5/024* (2006.01)
- *A61B 5/08* (2006.01)

(52) U.S. Cl.
CPC .............. *A61B 5/72* (2013.01); *A61B 5/7225* (2013.01); *A61B 5/7246* (2013.01); *A61B 5/7282* (2013.01); *A61B 5/742* (2013.01); *A61B 5/7405* (2013.01); *A61B 7/003* (2013.01); *A61B 7/04* (2013.01); *G06K 9/0053* (2013.01); *A61B 5/0002* (2013.01); *A61B 5/024* (2013.01); *A61B 5/0816* (2013.01); *A61B 5/7235* (2013.01)

(56) References Cited

U.S. PATENT DOCUMENTS

| | | | |
|---|---|---|---|
| 5,337,753 | A | 8/1994 | Lekhtman |
| 5,365,934 | A | 11/1994 | Leon |
| 5,558,096 | A | 9/1996 | Palatnik |
| 5,584,295 | A | 12/1996 | Muller |
| 6,210,344 | B1 | 4/2001 | Perin |
| 6,396,931 | B1 | 5/2002 | Malilay |
| 6,572,560 | B1 | 6/2003 | Watrous |
| 7,346,174 | B1 | 3/2008 | Smith |
| 8,172,764 | B2 | 5/2012 | Gregson |
| 8,491,481 | B2 | 7/2013 | Kabakov |
| 2006/0056641 | A1 | 3/2006 | Nadjar |
| 2006/0173713 | A1 | 8/2006 | Petro |
| 2008/0058607 | A1 | 3/2008 | Watrous |
| 2008/0109041 | A1* | 5/2008 | de Voir .............. A61B 5/04017 607/7 |
| 2011/0190665 | A1 | 8/2011 | Bedingham |
| 2011/0245630 | A1* | 10/2011 | St. Pierre .............. G06F 19/322 600/301 |
| 2011/0301427 | A1 | 12/2011 | Fu |
| 2012/0190303 | A1 | 7/2012 | Wong |
| 2012/0242501 | A1 | 9/2012 | Tran |
| 2013/0117207 | A1 | 5/2013 | Kim |
| 2013/0237773 | A1* | 9/2013 | An .......................... A61B 7/04 600/301 |
| 2013/0237793 | A1 | 9/2013 | Farrugia |
| 2013/0272528 | A1* | 10/2013 | Bushen ............... G06F 13/1663 381/18 |
| 2013/0310709 | A1* | 11/2013 | Ko .......................... A61B 7/02 600/586 |

FOREIGN PATENT DOCUMENTS

| | | |
|---|---|---|
| WO | WO 2008/097008 A1 | 8/2008 |
| WO | WO 2011/034843 A1 | 3/2011 |

OTHER PUBLICATIONS

Yan, Zhonghong et al.: *The Moment Segmentation Analysis of Heart Sound Pattern*; Computers Methods and Programs in Biomedicine, vol. 98, pp. 140-150 (Sep. 16, 2009) (11pages).

Marani, Roberto et al.: *High Quality Heart and Lung Auscultation System for Diagnostic Use on Remote Patients in Real Time*; The Open Biomedical Engineering Journal, vol. 4, pp. 250-256 (Jul. 29, 2010) (7 pages).

Search Report for International Application No. PCT/IB2014/059760 dated Nov. 4, 2014 (6 pages).

Written Opinion for International Application No. PCT/IB2014/059760 dated Nov. 4, 2014 (11 pages).

Canadian Office Action in Canadian Patent Application No. CA 2907020, dated Apr. 15, 2020 (3 pages).

\* cited by examiner

AUTOMATED DIAGNOSIS-ASSISTING MEDICAL DEVICES UTILIZING RATE/FREQUENCY ESTIMATION

CROSS-REFERENCE TO RELATED APPLICATIONS

This application claims the benefit of and priority to U.S. Provisional Patent Application No. 61/787,998, titled "Automated Diagnosis-Assisting Medical Devices Utilizing Rate/Frequency Estimation And Pattern Localization Of Quasi-Periodic Signals" and filed on Mar. 15, 2013, which is incorporated herein by reference in its respective entirety.

COPYRIGHT

A portion of the disclosure of this patent document contains material which, is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

Various aspects of the present disclosure relate to the estimation of the rate or frequency and to the localization of similar patterns in quasi-periodic signals. More specifically, for example, the signals are not limited to being quasi-periodic and are often overlaid with noise or other artifacts. More generally, some aspects relate to automated signal processing of sounds originating from various body structures for providing clinical referral conditions at a site, such as the patient's site.

BACKGROUND

Analyzing quasi-periodic signals is very common, e.g., analyzing sounds originating from the heart or lungs, and has long been a tool for evaluating conditions of subjects or patients. Since the existence of the stethoscope, the electrocardiogram device, and similar devices, such practices have been formalized. In the case of the stethoscope, for example, the sound is detected non-invasively at the surface of the skin and evaluated by a skilled practitioner. This is a standard screening method performed worldwide and called auscultation. Interestingly, auscultation is also one of the few remaining routine medical procedures in which the diagnosis is made purely by the medical professional who listens and interprets the sounds originating from the heart or lungs based solely on his or her training and experience.

With no objective and comparable means of evaluation, the quality of the subjective human diagnosis is solely dependent on the investigating medical professional, inevitably leading to a lack of objectivity and a high variability of findings between medical professionals. As such, making a diagnosis is vulnerable to human error and subjectivity due to a multitude of potential causes (e.g., stressful working environment, lack of sleep, etc.) associated with the medical profession. All of the above identified problems create a huge burden of responsibility for the medical professionals. Additionally, without an independent system in place that supports and documents the medical professionals' findings from the auscultation (including objective, clinically tested, investigator-independent, patient-specific parameters), the medical professionals lack an objective basis to defend their subjective findings.

Since the rise of high-speed computing, increasing attention has focused on analyzing digitized quasi-periodic signals through digital signal processing ("DSP") techniques. Often, the DSP techniques have been used simply for determining the rate, frequency, or steadiness of such signals. More recently, the DSP technique have also been used to determine pathological conditions of a medical subject.

The problem or challenge with such analyses lies in the reliable extraction and classification of significant features, often hidden in the recordings of such variable biological signals. This leads to the importance of proper or correct signal segmentation, which is often performed manually or sometimes automatically on good quality signals. In reality, recorded biological signals in a clinical environment are not of "good" quality, in which case existing systems struggle to yield reliable and robust results. For example, most current approaches of rate detection are simply triggered by the presence of a certain energy level in the signal, which is problematic in environments containing other noise or sounds, such as, for example, people walking or talking, other machines, traffic noise, etc. Other approaches are also detrimental because they require external input, such as, for example, electro cardiogram data, to achieve correct signal segmentation.

Therefore, there is a need, for example, for handling uncorrelated noise and variations in the periodicity of such variable input signals, and/or for estimating signal rates or frequencies, as well as recognizing and identifying locations of similar patterns. For example, such technology can be utilized as a standalone device or as part of a larger system for automated diagnoses of quasi-periodic signals.

SUMMARY OF THE INVENTION

According to an aspect of the present disclosure, a method or algorithm is disclosed that estimates a rate or frequency of quasi-periodic signals and localizes similar patterns in quasi-periodic signals without requiring high-end computing powers. Quasi-periodic signals are signals that can potentially be highly irregular while still containing some repeating, often hidden, features. Exemplary signals include biological signals that are concealed by noise and artifacts from various sources, such as originating internally (from a body structure) or externally (from the environment), and that are independent of the signal type or acquisition (e.g., electrical, mechanical, optical, acoustical, etc.). The signals are typically, but not necessarily limited to being quasi-periodic, and are often overlaid with noise or other artifacts.

Another aspect of the present disclosure is directed to determining a representative estimation of the rate of such signals, e.g., heart beat frequency or breathing frequency. The signal rate from biological sources is often a parameter of interest in clinical settings, but can also be utilized in subsequent or related signal processing stages to perform further analysis. The algorithm includes utilizing a combination of auto-correlation functions, tapering functions, and/or progressive signal splitting and statistical tools to analyze quasi-periodic signals.

Furthermore, yet another aspect of the present disclosure utilizes signal templates, e.g. a single representative heartbeat in a series of heartbeats or an analytical signal that shows similar features as the pattern of interest in the target signal, to search throughout the entire signal for locations where similar signal patters (or shapes) are found. The resulting locations are stored and returned. The algorithm utilizes a sequence of cross-correlation and windowing functions in combination with signal rate estimation that makes the algorithm robust against changes in periodicity, noise, and artefacts.

According to yet another aspect of the present disclosure, a method or algorithm is disclosed that changes traditional functions of electronic stethoscopes from a device typically capable of recording, storing, and manipulating data, into a device that automatically delivers diagnostic results for clinically relevant referral conditions directly to patient's site. By utilizing, for example, parallel system processing, involving novel algorithms, and physiological parameters that are optimized with findings from clinical studies, an embodiment of the present disclosure relates to a method of analyzing and diagnosing digital physiological signals that were recorded with commercially available electronic stethoscopes.

Figure 3:
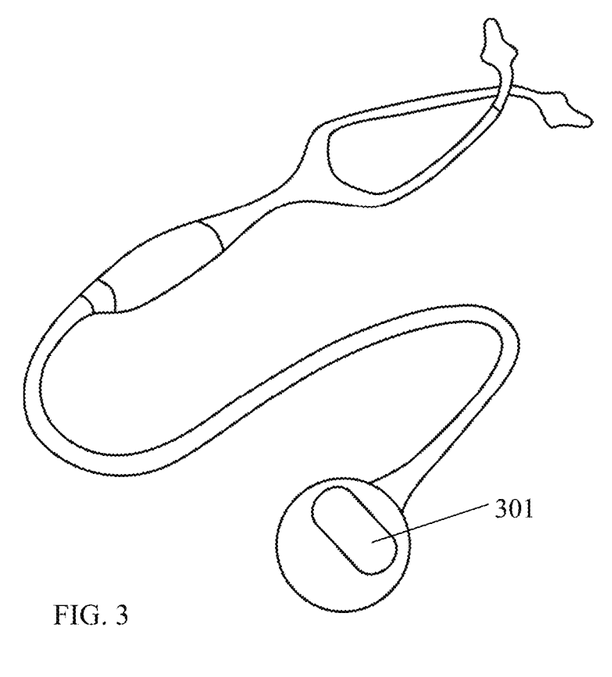
FIG. 3 is a representative illustration of an electronic stethoscope that includes a display for visual indication of a resulting diagnosis.
Figure 4:
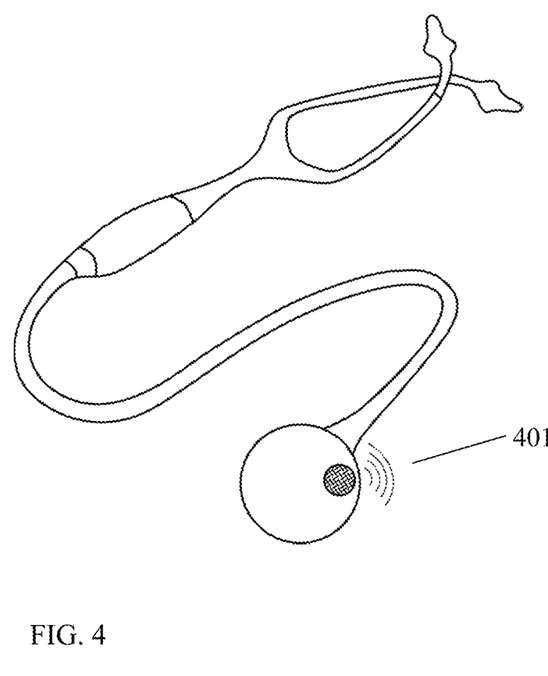
FIG. 4 is a representative illustration of an electronic stethoscope that acoustically indicates a resulting diagnosis.
Figure 5:
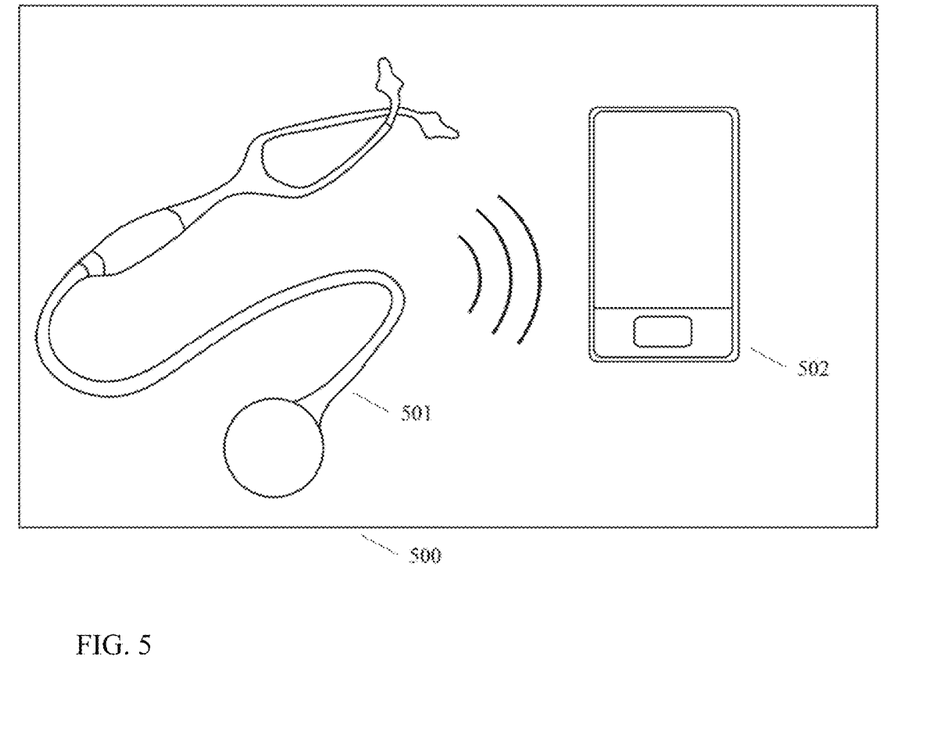
FIG. 5 is a representative illustration of an electronic stethoscope that is connected to an external, portable device (e.g., a small device, tablet, smartphone, etc.) for indication (visually, acoustically, or otherwise) of resulting findings including diagnosis suggestion.

According to yet another aspect of the present disclosure, a method of estimating a frequency of a quasi-periodic signal is performed directly by an electronic stethoscope as illustrated in FIG. 3 and FIG. 4. Alternatively, the method is performed by a small, external and portable device connected or linked to the stethoscope, as illustrated in FIG. 5 (e.g., a small device, tablet, smartphone, etc.), but that does not require high-end computing powers. The utilization of one or more aspects of the disclosed algorithm using standard computing resources, e.g., found in state-of-the-art smartphones or tablet computers, is possible due to various attributes of the algorithm, such as further described below.

According to one attribute, the algorithm uses methods like auto-correlation or cross-correlation, which can be computed very efficiently by using time-frequency conversion to perform such operations. Microprocessors often provide optimized implementations of such time-frequency conversions, such as Fast Fourier Transform ("FFT"), and, therefore, significantly boosting time-domain operations.

According to another attribute, the algorithm enables fast and efficient computation by using pre-trained classifiers (e.g., neural networks, support vector machines, Bayesian networks, etc.). The pre-trained classifiers facilitate new data to be classified with simple and computationally efficient operations (e.g., matrix multiplications). For this approach, parameters are determined with training data. For example, in reference to neural networks, weights and biases determined with training data. Or, in reference to support vector machines, the location of the support vectors in the hyperspace is determined with training data. Comprehensive and well classified training data is useful for a good pre-training of classifiers. The training data of the disclosed algorithm includes, for example, raw phonocardiogram data and/or corresponding diagnoses (obtained using, for example, echocardiography as the gold standard method for diagnosing heart defects). With a comprehensive training set, a classifier can be optimized (or, pre-trained) and applied to new data, which enables fast and efficient computations. In contrast, so-called lazy-learning methods use the whole available data set (stored locally) and compare new data against the whole training set for classification. The lazy-learning methods lead to higher space requirements for storing the training data set and/or to increased computational costs for performing the classification.

According to yet another attribute, the features of interest (or inputs to the classifier) are determined in advance by feature selection algorithms (e.g., sequential floating forward selection), which reduce feature space. Features are also analyzed using statistical tools such as a principal component analysis, which results in linearly uncorrelated variables and which further optimizes the feature space. Hence, only the most powerful and meaningful features are selected for the algorithm, increasing its computational efficiency and robustness against noise and outliers.

According to yet another aspect of the present disclosure, a method and/or system includes combining an electronic stethoscope with a portable device (FIG. 5) for automated analysis and diagnosis-support for stethoscope-based auscultation. The method and/or system utilizes one or more of the algorithms described below in reference to FIGS. 1, 2, and/or 6. The analysis is performed by the portable device, which provides results including a set of patient-specific parameters and/or indicators. The results are investigator independent and include medical and technical parameters, such as heart and/or breathing rate, heart and/or breathing rate variability, systolic and diastolic energy, signal curve, diagnosis suggestion, etc. At least some of these objective parameters and/or other results are displayed and/or stored on the portable device as a means for diagnosis support for the medical professional or other user.

Figure 7:
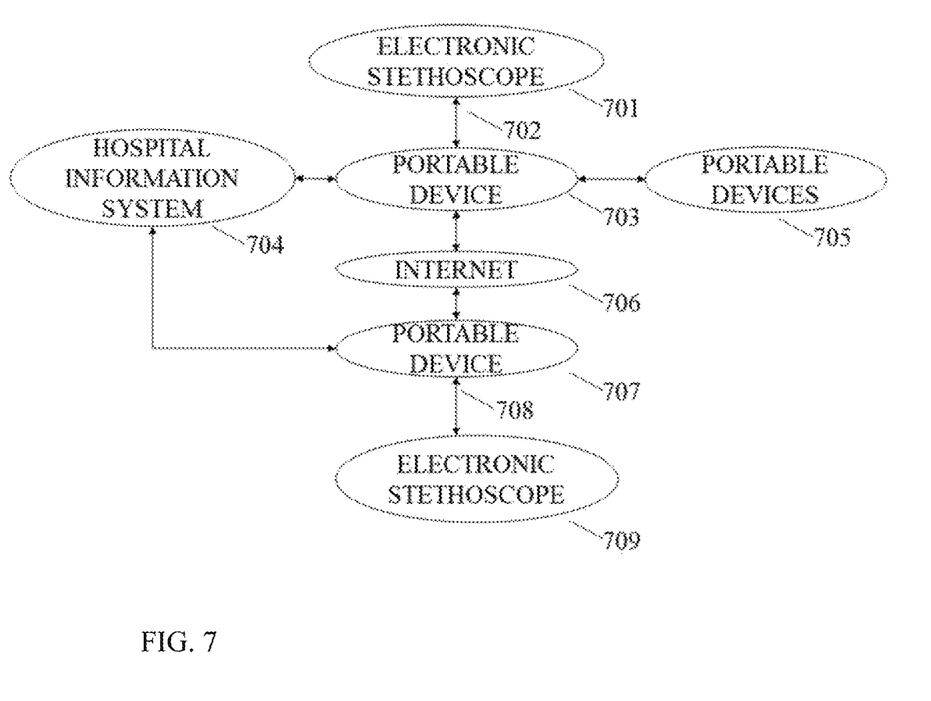
FIG. 7 outlines a bidirectional system architecture for achieving documentation, teaching, and/or bidirectional tele-auscultation.

According to yet another aspect of the present disclosure, a bidirectional system architecture is illustrated in FIG. 7 for enabling a device to be utilized for one or more of the following purposes:

(i) documentation purposes including, for example, saving all data and results in a common file format (e.g., PDF format), printing, emailing, bidirectional integration into a hospital information system ("HIS"), and/or efficient filing of all data and results to a patient's medical file;

(ii) teaching, training, research, and/or presentation purposes by wirelessly connecting the portable device to a single or multiple other portable devices that receive all data, including the results obtained with the utilization of one or more of the described algorithms; and/or (iii) bidirectional tele-auscultation for remote auscultation allowing the user to remotely control settings of an electronic stethoscope at a patient's site (e.g., change filters, adjust volumes, etc.), to communicate with a person operating the electronic stethoscope (e.g., instructing the person to change the position of the stethoscope), and to further provide documentation and HIS integration.

According to yet another aspect of the present disclosure, a bidirectional system architecture is disclosed as illustrated in FIG. 7 and in which the HIS is utilized to host or run one or more of the described algorithms. The system allows a user to access the system via a portable device or any computer connected to the HIS. Optionally, recorded signal data is uploaded and/or stored in the HIS. The data is analyzed by the HIS directly and/or the data is downloaded onto the portable device for later or remote analysis.

According to other aspects of the present disclosure, the device does not require any external input from medical professionals or other devices (e.g., ECG), does not require traditional auscultation techniques to be modified, does not require especially quiet environments (such as, for example, the holding of breath by the patient during auscultation), and/or does not require manual or semi-automated analysis by a medical professional. Alternatively, adding an external input by the user is optional and does not hinder the device from performing its tasks. In fact, the external input might potentially even increase the accuracy of the results.

By way of example, in reference to a phonocardiogram analysis, the age of the patient is a helpful parameter for narrowing down the range of likely heart rates and possible diseases (e.g., a specific classification of a heart murmur). A newborn, for example, usually has a heart rate greater than 100 beats per minute and the range of possible diseases is generally different than, for example, for a child greater than 2 years of age. One or more features of the present disclosure are beneficial to and enhance existing electronic stethoscopes by increasing their function as a medical device and informing medical staff within a short period of time whether physiological signals are healthy or require further medical attention. Thus, one or more features of the present disclosure can be utilized directly on an electronic stethoscope or in combination with an electronic stethoscope and a portable device, wherein computations and interaction (e.g., visualization of the findings) with medical staff are achieved through the portable device.

According to one embodiment of the present disclosure, a method is directed to processing a quasi-periodic signal and includes receiving, using a controller, a representation of a quasi-periodic signal, and removing, using the controller, a DC component from the received signal to produce a purely time-varying signal. The time-varying signal is filtered, using the controller, to produce a pre-processed signal, and at least a portion of a representation of the pre-processed signal is auto-correlated, using the controller, with itself. A corresponding auto-correlation output is stored in a memory device for the at least portion of the representation of the pre-processed signal. A biphasic tapering function is applied, using the controller, to the auto-correlation output, the tapering function including a time constant parameter that is a function of the quasi-periodic signal and producing a first maximum. A representation, based on the first maximum, is stored in the memory device as an indication of a rate or a frequency of the quasi-periodic signal.

According to another embodiment of the present disclosure, a system for processing a quasi-periodic signal includes a processor and a memory device stored with instructions that, when executed by the processor, cause the system to receive a representation of the quasi-periodic signal. A DC component is removed from the received signal to produce a purely time-varying signal. The time-varying signal is filtered to produce a pre-processed signal and at least a portion of a representation of the pre-processed signal is auto-correlated with itself. A biphasic tapering function is applied to the auto-correlation output, the tapering function including a time constant parameter that is a function of the quasi-periodic signal and producing a first maximum. A representation, based on the first maximum, is stored in the memory device as an indication of a rate or a frequency of the quasi-periodic signal.

According to yet another embodiment of the present disclosure, a method is directed to localizing a pattern in a quasi-periodic signal and includes estimating, using a controller, a rate or a frequency of a quasi-periodic signal. A search window is defined, using the controller, based on the estimated rate or frequency of the quasi-periodic signal. A starting position is defined, using the controller, in the received quasi-periodic signal, the starting position corresponding to a first maximum. A portion of the quasi-periodic signal in the search window is cross-correlated, using the controller, with a template signal pattern to be matched to produce a second maximum that is defined by the controller as a new starting position. The new starting position is stored using the controller.

According to yet another embodiment of the present disclosure, a system is directed to localizing a pattern in a quasi-periodic signal and includes a processor and a memory device. The memory device has stored instructions that, when executed by the processor, cause the system to estimate a rate or a frequency of a quasi-periodic signal and define a search window based on the estimated rate or frequency of the quasi-periodic signal. A starting position is defined in the received quasi-periodic signal, the starting position corresponding to a first maximum. A portion of the quasi-periodic signal in the search window is cross-correlated with a template signal pattern to be matched to produce a second maximum that is defined by the controller as a new starting position. The new starting position is stored.

According to yet another embodiment of the present disclosure, a system is directed to processing a quasi-periodic signal and includes an electronic stethoscope for recording a quasi-periodic signal, a processor, and a memory device with stored instructions. When executed by the processors, the stored instructions cause the system to receive a representation of the quasi-periodic signal, and to remove a DC component from the received signal to produce a purely time-varying signal. The time-varying signal is filtered to produce a pre-processed signal, and at least a portion of a representation of the pre-processed signal is auto-correlated with itself. A corresponding auto-correlation output is stored in a memory device for the at least portion of the representation of the pre-processed signal. A biphasic tapering function is applied to the auto-correlation output, the tapering function including a time constant parameter that is a function of the quasi-periodic signal. The tapering function further produces a first maximum. A representation, based on the first maximum, is stored in the memory device as an indication of a rate or a frequency of the quasi-periodic signal.

The foregoing and additional aspects and embodiments of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

These and other features of exemplary implementations of the present disclosure will become apparent from the description, and the accompanying drawings. According to common practice, various features of the drawings are not to scale but are purposefully modified arbitrarily for improved clarity wherein.

DETAILED DESCRIPTION OF THE INVENTION

Figure 1:
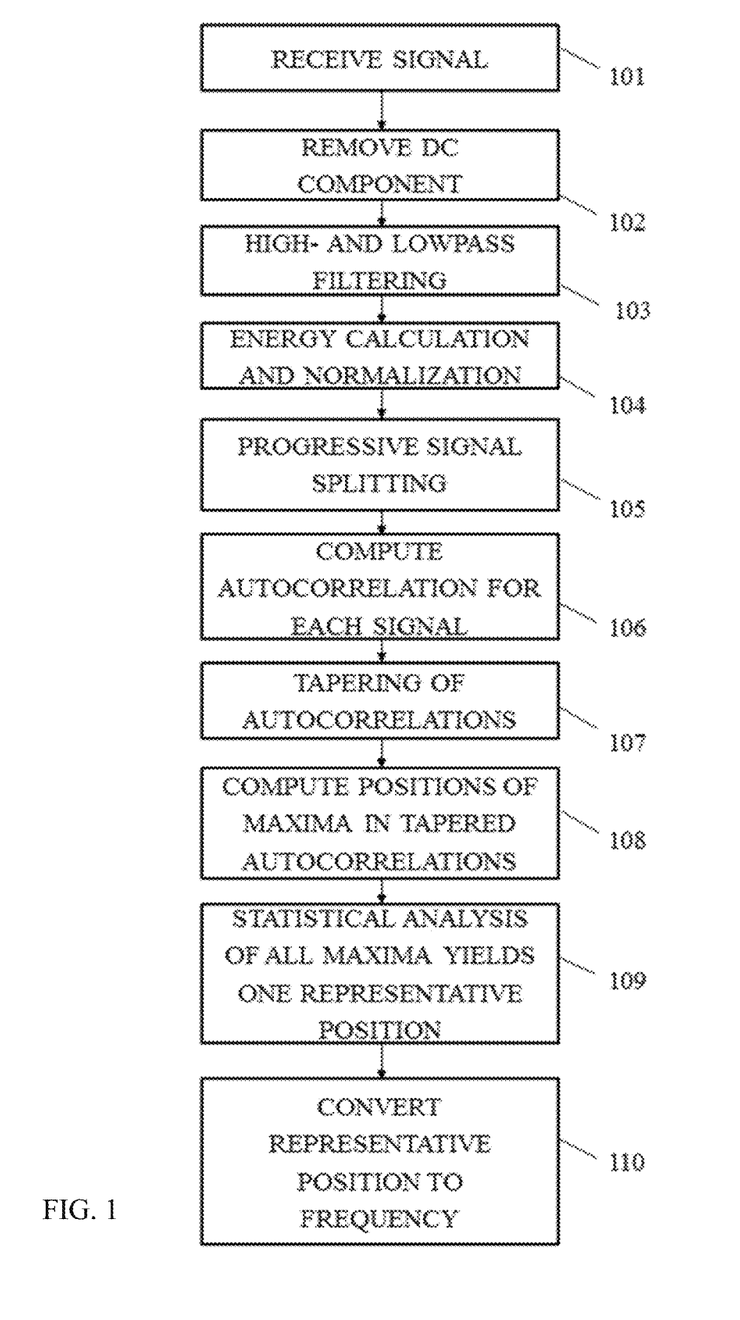
FIG. 1 is a diagrammatic illustrating a process of rate or frequency estimation in quasi-periodic signals.

Referring to FIG. 1, a diagrammatic illustrates a rate/frequency estimation algorithm in accordance with one aspect of the present disclosure. At 101, a quasi-periodic input signal, such as an acoustical signal indicative of a physiological rhythm (e.g., heartbeat, respiration), is loaded. At 102, a DC component is removed from the input signal, s, according to $s_{DCrem}=s-\text{mean}(s)$, where $$\text{mean}(x) = \frac{1}{N}\sum_{n=1}^{N} x(n)$$

is the mean operator, $s_{DCrem}$ is the input signal having its DC component removed, and N is the length of x.

At 103, filtering of the input signal is applied to produce a pre-processed signal that emphasizes the quasi-periodic patterns of the signal for rate estimation (e.g., the heart sound S1 and S2 in a phonocardiogram). The filtering is performed with a standard band-pass filter (high-pass filtering and/or low-pass filtering) or with wavelet filtering. In accordance with wavelet filtering, the signal is decomposed into detail and approximation coefficients, and, as such, thresholding of the detail coefficients with subsequent reconstruction of the signal enables noise removal. Corresponding cut-off frequencies, filter types, and threshold levels in 103 are dependent on the type of input signal. Examples of input signals include heart sounds, breathing sounds, bowel sounds, quasi-periodic signals, etc. Furthermore, threshold levels are not directly dependent on the type of input signal, but are computed specifically for each input signal.

At 104, from the now pre-processed signal, signal energy is calculated and normalized, e.g., $$s_{norm} = s_{filt} \bigg/ \sqrt{\frac{1}{n}\sum_{n=1}^{N} s_{filt}(n)^2},$$

where the denominator corresponds to the root mean square of the signal, where $s_{filt}$ is the filtered, pre-processed signal, and N denotes the length of $s_{filt}$. If permitted by signal length, at 105 the signal energy is split into progressively smaller time domains, by continuously dividing the entire pre-processed signal energy in halves, thirds, quarters, etc. The splitting of the signal energy continues as long as the length of the smallest resulting domain contains sufficient information for a meaningful analysis.

For example, if a medical professional is interested in analyzing heartbeats, the size of the smallest domains would have to be large enough to cover the main features of a few heartbeats. Every resulting signal energy domain is stored accordingly in a memory device of a computer or computing device.

At 106, for each domain of the energy the auto-correlation of the domain itself is computed and stored, yielding auto-correlations for every domain. A normalized version of the auto- and cross-correlation is used, which compensates for the differences in signal magnitudes and properly correlates a shorter signal with a longer one. This normalized version divides the results of the correlation by the energy of the parts of the signals that were effectively correlated.

First, the shorter signal $s_2$ is zero-padded to have equal length as the longer signal $s_1$. Second, the standard cross-correlation of $s_1$ and $s_2$ is performed by $temp=s_1 \star s_2$, where temp includes only the positive terms, i.e., the second half, of the standard cross-correlation ($\star$ is the cross-correlation operator). Third, the masked energy correlation, $en_m$, is computed according to $en_m=s_1^2 \star \text{ones}(\text{length}(s_2))$, where the latter term represents a rectangular window with the length equal to the length of the shorter signal $s_2$. Fourth, the result of the normalized cross-correlation, $res_{cc}$, is computed according to $$res_{cc} = \frac{temp}{\text{abs}(\sqrt{en_m}) * \text{abs}(\sqrt{s_2, s_2})},$$

where the dot product $s_2.s_2$ is used. Since a convolution in the time domain corresponds to a multiplication in the frequency domain, efficient computation is achieved, e.g., computing auto-correlation of $s(t)$, $res_{ac}=\text{IFFT}(F_s(f)*F_s*(f))$, where $F_s(f)=\text{FFT}(s(t))$ is the FFT of $s(t)$, $F_s*(f)$ denotes the complex conjugate, and IFFT performs the Inverse Fast Fourier Transform.

At 107, a tapering function is applied to every auto-correlation to amplify the relevant maximum in the auto-correlation. To amplify the first maximum representing the rate or frequency, the tapering function is biphasic, where the two phases are selected depending on the input signal but can generally include a rising edge followed by a trailing edge. The biphasic function is necessary because the auto-correlation function of quasi-periodic signals features multiple peaks, and the biphasic nature of the tapering function allows the selection of the most probable (single) peak (by tapering other, more improbable peaks) representing the period of interest. The tapering function additionally includes a time constant as a parameter that also depends on the input signal and that is pre-determined from, for example, values reported in the literature (e.g., average breathing/heart rates for different patient groups) or suitable clinical data if available.

An example of a biphasic tapering function, $f_{taper}(t)$, is the following exponential function:

$$f_{taper}(t) = \frac{t}{T_c} e^{-\frac{t}{T_c}},$$

where $T_c$ is a time constant and t is the time. The two phases of the tapering function are reflected in the first term, which represents a linear increase (e.g., a rising edge or phase), and the second term representing an exponential decline (e.g., a trailing edge or phase). Although other biphasic tapering functions could be used to amplify the maximum in the auto-correlation representing the period time, the exemplary exponential form described above is suitable for estimating a frequency specific in phonocardiograms, based on determinations of clinical phonocardiogram data covered in substantial amount of noise.

The exemplary biphasic tapering function yielded the best results for selecting the single peak in the auto-correlation function that correlates best with the heart rate of the patient. The maximum of this particular tapering function is at $t=T_c$ (as can be seen by setting the first derivative of $f_{taper}$ to zero, $$f'_{taper} = \frac{T_c - t}{T_c^2} e^{-t/T_c} = 0).$$

Furthermore, $T_c$ is computed by $T_c=1/f$, where f is the most probable frequency in the signal, which is determined from reported values in the literature or clinical data. By way of example, for very young children (during the first few months of life) a time constant in the range of 0.6 to 0.3 is appropriate and corresponds to an average heart rate between about 100-200 beats per minute.

At 108, the positions of the maxima in the tapered auto-correlations are computed and stored in a memory device. At 109, standard statistical measures such as, for example, mean, median, standard deviation, variance, or other tools (e.g., maximum likelihood estimation) are utilized to determine one representative position for all maxima. Finally, at 110 the one representative position of all maxima of the tapered auto-correlations is converted, yielding the representative signal rate or signal frequency.

Figure 2:
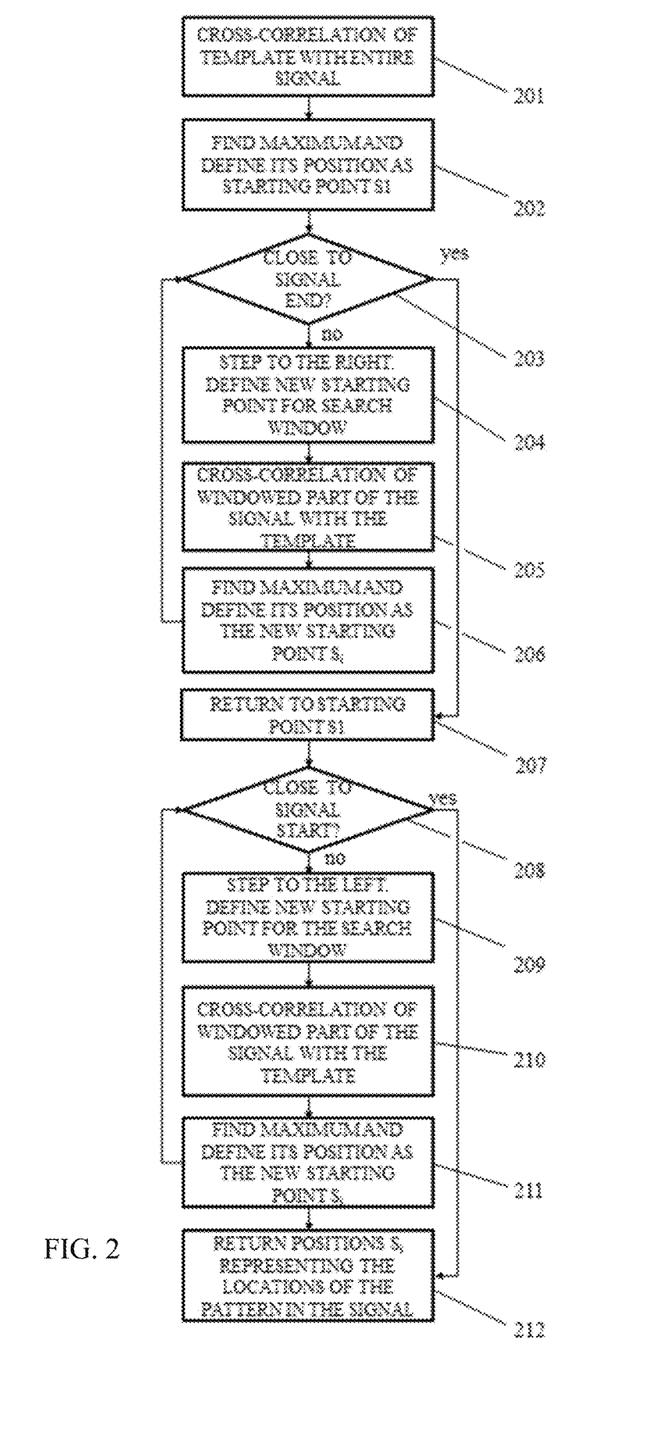
FIG. 2 is a flowchart illustrating a process for localization of similar patterns in quasi-periodic signals.

Referring to FIG. 2, a flowchart is directed to outlining a process for the localization of similar patterns in quasi-periodic signals. This process does not require any external input, such as an ECG signal for segmentation or other purposes. The localization algorithm calls for a template representing a signal pattern to be matched to similar patterns throughout the signal. For example, in a physiological signal of a series of heartbeats, the template can be one of the heartbeats in the series.

The template can also be an analytical signal that shows similar features as the pattern of interest in the target signal. For example, for a phonocardiogram, a primitive template includes two waveforms representing S1 and S2 that are shifted in time, depending on the estimated heart rate. Examples of such waveforms that feature certain similarities with S1 and S2 include the Shannon wavelet $$\Psi_{shannon}(t) = \text{sinc}\left(\frac{t}{2}\right)\cos\left(\frac{3\pi t}{2}\right)$$

and the real part of the Morlet wavelet $$\Psi_{morlet}(t) = c_\sigma \pi^{-\frac{1}{4}} e^{-\frac{t^2}{2}} (e^{i\sigma t} - \kappa_\sigma),$$

where $c_\sigma$ and $\kappa_\sigma$ are constants.

At 201, the template is cross-correlated with the entire input signal, such as a physiological signal. The maximum of the cross-correlation represents the best match of the template with the signal, and at 202 the position of the maximum is defined as the starting position S1 for the localization algorithm.

At 203, the localization algorithm checks if the remaining signal length after the S1 position is long enough to contain the search window specified at 204. If yes, the algorithm steps to the right of S1 (forward in time) where a new starting point is defined for a search window, shown at 204. The step size, as well as the size of the search window in 204, is based on an estimated signal frequency or signal rate, which, for example, is estimated with the algorithm described in FIG. 1 above.

At 205, the windowed part of the signal is cross-correlated with the template. At 206, the position of the maximum in the cross-correlation is computed and stored in a memory device as the new starting point $S_i$. The maximum represents the best match of the template with the signal within the search window. Next, the localization algorithm goes back to 203 to check if it has arrived close to the signal end. If not, modules 204-206 are repeated. If yes, the algorithm goes back to the starting position S1, according to 207.

Throughout modules 208-211, the localization algorithm performs the same operations as in modules 203-206, but instead of stepping to the right the algorithm keeps stepping to the left of S1 (back in time). The step size as well as the size of the search window throughout modules 208-211 are again based on an estimated signal frequency or signal rate, but are not necessarily the same as at modules 203-206. Examples of such step sizes suitable for auscultation data from new-borns are $0.6*T_p$ for the start and $1.8*T_p$ for the end of the search window to the right, and $1.4*T_p$ and $0.2*T_p$ for the length of the search window, where $$T_p = \frac{1}{f}$$

is the period.

When the localization algorithm arrives at a position too close to the signal start (the left end of the signal), where the remaining part of the signal to the left is too short to contain a new search window, 208 ensures that the localization algorithm jumps to 212, where all stored positions $S_i$ are returned. The positions $S_i$ represent the locations of the patterns throughout the signal that match the template. This process can be repeated for different patterns of the same input signal. The input signal is not limited to being quasi-periodic and can include a significant amount of noise or artefacts. Furthermore, this process is independent of the type of signal or signal acquisition (e.g., electrical, mechanical, optical, acoustical, etc.).

Advantages of using a search window include that the signal does not have to be strictly periodic and repeating patterns can still be found. Moreover, the window restricts the search area to a reasonable size, ensuring that patterns covered in noise can also be detected using a template containing similar features as the desired pattern. Ultimately, the lengths and positions of the search windows depend on the signal, keeping in mind that longer windows allow the signal to be more irregular while making the pattern detection in noisy signals more complicated. The position and length of the window is selected such that it does not contain two or more of the patterns of interest, otherwise one of the multiple patterns might be skipped.

Figure 6:
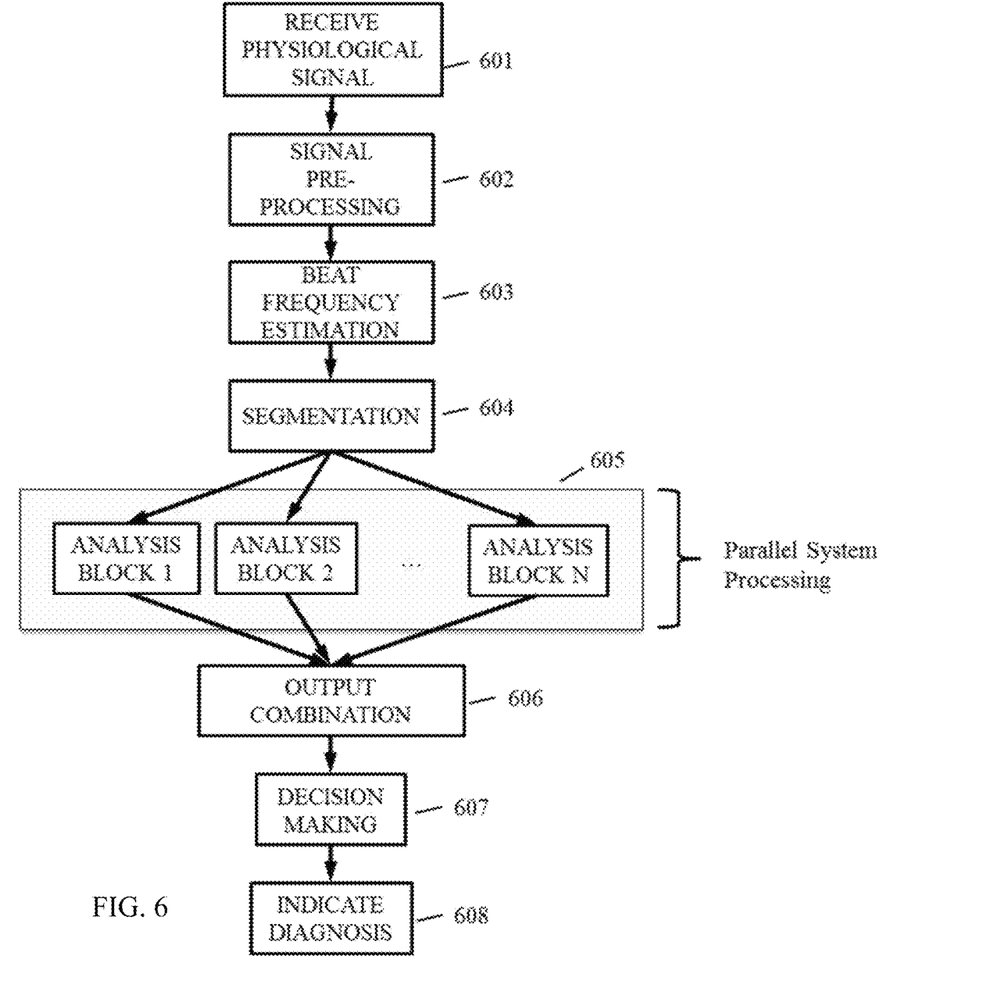
FIG. 6 is a flowchart illustrating an exemplary method of digital signal processing of physiological signals.

Referring to FIG. 6, a flow chart illustrates modifying an electronic stethoscope into a diagnosis-assisting tool providing additional medically relevant information regarding the physiological signal. At 601, a quasi-periodical, digital physiological signal is received from an electronic stethoscope. Then, the signal is pre-processed (e.g. filtered, normalized, etc.) at 602.

The beat frequency is estimated at 603 using, e.g., the algorithm illustrated in FIG. 1 and used in the segmentation stage at 604, which is also illustrated in FIG. 2. This segmentation at 604 yields the segments of interest of the signal, e.g., the systole and/or diastole of each heart beat, and/or the inhale and/or exhale phase of a breath.

In a parallel system processing stage, for example, at 605, various analysis modules operating in both the frequency and the time domain are applied to extract features of the segments obtained at 604. For example, such features include an Energy Analysis, Timing Features (e.g., Heart Rate Variability, Duration of S1/Systole/S2/Diastole, etc.), Fourier Transform, Short Time Fourier Transform, Higher Order Statistics (e.g., Bispectra, Gaussian Mixture Models, etc.), Discrete and Continuous Wavelet Analysis, Fractal Dimension Analysis, Stockwell-Transform, Error Entropy Analysis, etc. The output of the parallel modules at 605 is combined at 606 and passed to 607, where the output is used in a decision making stage. If external data, such as patient age or certain aspects of patient's medical history, is added, classification of specific pathologies might yield increasing accuracy.

The output of 607 is forwarded to 608 where the diagnosis is indicated to the user on an electronic display device. The diagnosis is indicated, for example, via a binary output, via probabilities, via an acoustic signal, and/or via a visual interface. The visual interface can include a detailed listing of the findings, including a diagnosis suggestion, all of which are optionally stored in a memory device on an electronic stethoscope or shared, stored or printed through other means as described above.

Additionally, still referring to FIG. 6, a basic structure of a digital signal processing is utilized by one or more aspects of the invention. Parallelization, in combination with one or more of the above described algorithms and in combination with specific parameters obtained through clinical studies enable a fully automated analysis without requiring any external input in addition to the physiological signal itself (although external data and/or parameters can be optionally added). The diagnostic result is revealed directly on the electronic stethoscope (e.g., FIGS. 3-5) or the portable device that is connected to the electronic stethoscope (e.g., on display 502 of FIG. 5), either visually (through a display 301, 502) or acoustically (e.g., sound emitter 401).

Some or all modules described above, which have been described by way of example herein, represent one or more algorithms that correspond to at least some instructions executed by one or more controllers to perform the functions or modules disclosed. Any of the methods or algorithms or functions described herein can include machine or computer-readable instructions for execution by a processor, controller, computer, and/or any other suitable processing or computing device. Any algorithm, software, and/or method disclosed herein can be embodied as a computer program product having one or more non-transitory tangible medium or media, such as, for example, a flash memory, a CD-ROM, a floppy disk, a hard drive, a digital versatile disk ("DVD)", or other memory devices. However, persons of ordinary skill in the art will readily appreciate that the entire algorithm and/or parts thereof can alternatively be executed by a device other than a controller and/or embodied in firmware or dedicated hardware (e.g., it can be implemented by an application specific integrated circuit ("ASIC"), a programmable logic device ("PLD"), a field programmable logic device ("FPLD"), discrete logic, etc.).

Referring to FIG. 5, illustrates a method or system for automated analysis and diagnosis-support for stethoscope-based auscultation. An automated analysis and diagnosis-support system 500 includes an electronic stethoscope 501 with signal transmitting capabilities, which include, for example, an integrated Bluetooth transmitter and/or an appropriate transmitter for transmitting signals directly connected (e.g., via an audio jack) to the electronic stethoscope 501. The transmitter is capable of converting an analog signal to a digital signal and is optionally capable of encrypting the signal.

For example, heart sounds are transmitted to a processing unit 502, which can be included in a smartphone, a tablet, a computer, etc. The processing unit 502 automatically analyzes the transmitted signal with the utilization of one or more of the algorithms described above. The analysis yields a set of patient-specific parameters/indicators and results, including medical and technical parameters such as heart/breathing rate, heart/breathing rate variability, systolic and diastolic energy, signal curve, diagnosis suggestion (e.g., through probabilities or binary output), etc. All or a selection of these objective parameters and results are displayed and/or stored on the portable device as a means for diagnosis support for the medical professional.

Referring to FIG. 7, a bidirectional system architecture is illustrated for use with one or more of the algorithms described above for analyzing a signal, enabling a portable device 703 to be utilized for (i) documentation, (ii) teaching, and/or (iii) bidirectional tele-auscultation purposes.

In reference to documentation, items 701-704 illustrate utilizing an automated, analysis and diagnosis-support system 500 for documentation purposes. All data and results are saved as a common file type (e.g., PDF format) on the portable device 703, printed, and/or emailed. A bidirectional interface between the portable device 703 and the HIS 704 allows for retrieving of patient data from the HIS if required by the medical professional. The bidirectional interface further allows efficient filing of all data and results to the patient's medical file.

In reference to teaching, items 701-703 and 705 illustrate utilizing the automated, analysis and diagnosis-support system 500 for stethoscope-based auscultation as described above. The teaching, which is optionally directed to achieving training, research, and/or presentation objectives, is achieved by wirelessly connecting the portable device 703 to a single or multiple other portable devices 705. The portable devices 705 receive all data including the findings of the analysis system. According to one example, a professor teaches medical students the art of auscultation by performing auscultation using the electronic stethoscope 701 on one student and transmitting all related data and results of the system on the portable device 703 to the portable devices 705 of other students.

In reference to bidirectional tele-auscultation, items 701-703 and 706-709 illustrate a possibility for utilizing the automated, analysis and diagnosis-support system for stethoscope-based auscultation remotely through bidirectional tele-auscultation. In such a scenario, the data is transmitted from the first electronic stethoscope 701 (e.g., operated by a nurse or by the patient himself), through a data link 702 to the portable device 703. The data is further transmitted through a data connection 706 (e.g., the Internet) to a second portable device 707 (operated, e.g., by the medical professional performing the auscultation), and optionally through another data link 708 to a second electronic stethoscope 709 (operated, e.g., by the medical professional performing the auscultation).

In the above scenario, the first portable device 703 performs the required transmitting functions (with no analysis of the signal), and the second portable device 709 has the automated, analysis and diagnosis-support system for stethoscope-based auscultation running. The bidirectionality of this pathway (701-703 and 706-709) allows the medical professional operating the second portable device 707 to control the settings of the electronic stethoscope 701 (e.g., change filters, adjust volumes, etc.) and to communicate with the person operating the electronic stethoscope through the first stethoscope 701 or the portable device 703 (e.g., instructing the person to change the position of the stethoscope). Documentation and HIS integration are options in the scenario.

Optionally, the automated analysis and diagnosis-support system illustrated in FIG. 5 is installed and/or hosted by the HIS (e.g., HIS 704 of FIG. 7) and the user accesses the HIS via a portable device (e.g., portable devices 703, 707 of FIG. 7) or via a computer connected to the HIS. In such a case, the recorded signal data is optionally uploaded and/or stored in the HIS and is analyzed in the HIS directly utilizing one or more of the algorithms described above, and/or the data is downloaded onto the portable device for later or remote analysis utilizing one or more of the algorithms described above.

By way of a specific example, a medical professional uses an electronic stethoscope while medically evaluating a 10 year-old patient. The electronic stethoscope includes a communication input for connecting with a portable device. The medical professional connects the portable device (e.g., a smartphone) (a) to the hospital information system to receive the patient's medical data (e.g., age, medical history, etc.) and (b) to the electronic stethoscope. The communication input of the electronic stethoscope includes, for example, a built-in Bluetooth chip or an external Bluetooth transmitter connected an audio jack.

During the medical evaluation in which auscultation is performed, the electronic stethoscope records an acoustic heart signal while the medical professional listens to the heart sound. The electronic stethoscope converts the acoustic heart signal from an analog format into a digital format and transfers the digitized signal to the smartphone. The smartphone receives the digitized signal and processes it, including removing the DC component, filtering, etc.

After the processing of the digitized signal, the smartphone estimates the heart rate by partitioning the signal, auto-correlating the individual parts, applying a tapering function to each autocorrelation, and statistically analyzing the maxima of all autocorrelations. Then, the heart rate serves as the input for the segmentation stage, where a representative template (e.g., a template pre-stored on the smartphone) is correlated with the digitized signal to find the best matches of this template in the digitized signal within defined search windows.

The segmentation results from the previous modules are used in a feature extraction stage, where characteristic properties (or features) from the digitized signal are extracted (e.g., via Fourier Transform, Gaussian Mixture Models, Energy Analysis, etc.). These features serve as the input for a decision stage, in which the features are classified, for example, via Multilayer Perceptrons, Support Vector Machines, and/or a combination/cascade of such classifiers. The classifiers yield a diagnosis suggestion and/or a set of patient-specific parameters that are displayed for the medical professional via the smart phone. Results are optionally stored on the smart phone, and/or printed, sent via e-mail, and/or stored in the hospital information system.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A method for determining a rate or frequency of a quasi-periodic signal obtained from a portable electronic device to suggest a diagnosis finding or suggestion, the method comprising:
   receiving, using a controller, a representation of a quasi-periodic signal obtained from a portable electronic device configured to detect a heartbeat or a respiration;
   removing, using the controller, a DC component from the received signal to produce a purely time-varying signal;
   filtering, using the controller, the time-varying signal to produce a pre-processed signal;
   auto-correlating, using the controller, at least a portion of a representation of the pre-processed signal with itself and storing in a memory device a corresponding auto-correlation output for the at least a portion of the representation of the pre-processed signal;
   applying, using the controller, a biphasic tapering function to the auto-correlation output, the biphasic tapering function including a linear increase phase and an exponential decline phase and a time constant parameter that is a function of the quasi-periodic signal, the biphasic tapering function producing a first maximum, the time constant parameter being in a range of 0.6 to 0.3;
   storing in the memory device a representation, based on the first maximum, as an indication of a rate or a frequency of the quasi-periodic signal, wherein the representation of the quasi-periodic signal includes one or more of a heartbeat rate of a heartbeat and a respiration rate, and wherein the quasi-periodic signal is a phonocardiogram of the heartbeat or respiration;
   defining, using the controller, a search window having a width based on the stored representation as the indication of the rate or the frequency of the quasi-periodic signal;
   defining, using the controller, the first maximum as a starting position;
   cross-correlating, using the controller, at least a portion of the quasi-periodic signal in the search window including the starting position with a template signal pattern to be matched to produce a second maximum;
   determining using the controller a second representation as the indication of the rate or the frequency of the quasi-periodic signal based on at least the first maximum and the second maximum;
   causing the second representation to be displayed on an electronic display device, the second representation indicating the rate or the frequency of the detected heartbeat or the respiration;
   using the detected heartbeat or the respiration to suggest an automated diagnosis suggestion or finding relating to the detected heartbeat or the respiration, wherein the automated diagnosis suggestion or finding related to finding the detected heartbeat includes a heart defect or a heart murmur, and wherein the automated diagnosis or finding related to finding the detected respiration includes a breathing defect; and
   causing the diagnosis suggestion or finding to be displayed or communicated.

2. The method of claim 1, further comprising sharing, via a data connection, the stored representation as the indication of the rate or the frequency with a hospital information system.

3. The method of claim 2, further comprising:
   retrieving, using the controller, a patient list from the hospital information system;
   selecting, using a selection input, a patient from the patient list;
   obtaining raw auscultation data from the patient;
   determining, using the controller, patient specific parameters based on the raw auscultation data; and
   transferring, via the data connection, to the hospital information system one or more of patient data, the raw auscultation data obtained from the patient, the patient specific parameters, and a diagnosis suggestion.

4. The method of claim 1, further comprising:
obtaining raw auscultation data of the quasi-periodic signal;
sending, via a data connection, the raw auscultation data of the quasi-periodic signal to a hospital information system;
analyzing, using another controller of the hospital information system, the raw data; and
storing, on a memory device of the hospital information system, results of the analysis for later review by a medical professional.

5. The method of claim 1, wherein the filtering is wavelet filtering in which the signal is decomposed into detail and approximation coefficients.

6. The method of claim 1, further comprising splitting, using the controller, the pre-processed signal into progressively smaller time domains.

7. The method of claim 1, wherein the producing of the first maximum includes utilizing statistical measures.

8. The method of claim 1, further comprising converting representative positions of all maxima including the first maximum and the second maximum to indicate the rate or the frequency of the quasi-periodic signal.

9. A system for determining a rate or frequency of a quasi-periodic signal obtained from a portable electronic device to support a diagnosis finding or suggestion, the system comprising:
a processor; and
a memory device with stored instructions that, when executed by the processor, cause the system to:
receive a representation of the quasi-periodic signal obtained from a portable electronic device configured to detect a heartbeat or a respiration,
remove a DC component from the received signal to produce a purely time-varying signal,
filter, the time-varying signal to produce a pre-processed signal,
auto-correlate, at least a portion of a representation of the pre-processed signal with itself,
store in the memory device a corresponding auto-correlation output for the at least portion of the representation of the pre-processed signal,
apply a biphasic tapering function to the auto-correlation output, the tapering function including a linear increase phase and an exponential decline phase and a time constant parameter that is a function of the quasi-periodic signal, the tapering function producing a first maximum, the time constant parameter being in a range of 0.6 to 0.3,
store in the memory device a representation, based on the first maximum, as an indication of a rate or a frequency of the quasi-periodic signal, wherein the representation of the quasi-periodic signal includes one or more of a heartbeat rate and a respiration rate, and wherein the quasi-periodic signal is a phonocardiogram of the heartbeat or respiration,
define a search window having a width based on the stored representation as the indication of the rate or the frequency of the quasi-periodic signal;
define the first maximum as a starting position;
cross-correlate at least a portion of the quasi-periodic signal in the search window including the starting position with a template signal pattern to be matched to produce a second maximum;
determine a second representation as the indication of the rate or the frequency of the quasi-periodic signal based on at least the first maximum and the second maximum; and
cause the second representation to be displayed on an electronic display device, the second representation including the rate or the frequency of the detected heartbeat or the respiration to support an automated diagnosis suggestion or finding relating to the detected heartbeat or the respiration, the diagnosis suggestion or finding relating to the detected heartbeat including a heart defect or a heart murmur, and the diagnosis suggestion or finding relating to the detected respiration including a breathing defect.

10. The system of claim 9, wherein the memory device further causes the system to share, via a data connection, the stored representation as the indication of the rate or the frequency with a hospital information system.

11. The system of claim 10, wherein the memory device further causes the system to:
retrieve a patient list from the hospital information system;
select a patient from the patient list;
obtain raw auscultation data from the patient;
determine patient specific parameters based on the raw auscultation data; and
transfer to the hospital information system one or more of patient data, the raw auscultation data, the patient specific parameters, and a diagnosis suggestion.

12. The system of claim 9, wherein the memory device further causes the system to:
obtain raw auscultation data of the quasi-periodic signal;
send the raw auscultation data of the quasi-periodic signal to a hospital information system;
analyze the raw data at the hospital information system; and
store results of the analysis at the hospital information system for later review by a medical professional.

13. The system of claim 9, wherein the filtering is wavelet filtering in which the signal is decomposed into detail and approximation coefficients.

14. The system of claim 9, further comprising splitting, using the controller, the pre-processed signal into progressively smaller time domains.

15. The system of claim 9, wherein the memory device further causes the system to utilize statistical measure for producing the first maximum.

16. The system of claim 9, wherein the memory device further causes the system to convert representative positions of all maxima including the first maximum and the second maximum to indicate the rate or the frequency of the quasi-periodic signal.

* * * * *

UNITED STATES PATENT AND TRADEMARK OFFICE
CERTIFICATE OF CORRECTION

PATENT NO. : 10,856,811 B2
APPLICATION NO. : 14/209919
DATED : December 8, 2020
INVENTOR(S) : Andreas Schriefl It is certified that error appears in the above-identified patent and that said Letters Patent is hereby corrected as shown below:

On the Title Page

At Item (72): Inventor, please delete "(AU)" and insert --(AT)-- therefor.

Signed and Sealed this
Nineteenth Day of January, 2021

Andrei Iancu
*Director of the United States Patent and Trademark Office*